(12) United States Patent
Palmisano

(10) Patent No.: US 6,604,527 B1
(45) Date of Patent: Aug. 12, 2003

(54) MANDIBULAR ADVANCEMENT DEVICE

(76) Inventor: Richard George Palmisano, 178/18 Waverley Street, Bondi Junction, New South Wales 2022 (AU)

( * ) Notice: Subject to any disclaimer, the term of this patent is extended or adjusted under 35 U.S.C. 154(b) by 0 days.

(21) Appl. No.: 09/743,086

(22) PCT Filed: Jul. 6, 1999

(86) PCT No.: PCT/AU99/00547

§ 371 (c)(1),
(2), (4) Date: Mar. 7, 2001

(87) PCT Pub. No.: WO00/01317

PCT Pub. Date: Jan. 13, 2000

(30) Foreign Application Priority Data

Jul. 6, 1998 (AU) .............................. PP 4505

(51) Int. Cl.[7] .................................. A61F 5/56
(52) U.S. Cl. ................. 128/848; 128/859; 128/861
(58) Field of Search ............................... 128/846, 848, 128/859–862; 433/6; 602/902

(56) References Cited

U.S. PATENT DOCUMENTS

| 4,472,138 | A | | 9/1984 | Howe | 433/19 |
|---|---|---|---|---|---|
| 5,003,994 | A | | 4/1991 | Cook | 128/848 |
| 5,324,196 | A | | 6/1994 | Magill | 433/19 |
| 5,683,244 | A | | 11/1997 | Truax | 433/6 |
| 5,823,193 | A | * | 10/1998 | Singer | 602/902 |
| 5,829,441 | A | * | 11/1998 | Kidd | 128/861 |
| 5,884,628 | A | * | 3/1999 | Hilsen | 128/848 |
| 6,055,986 | A | * | 5/2000 | Meade | 128/859 |

FOREIGN PATENT DOCUMENTS

| DE | 29514984 | 10/1996 |
|---|---|---|
| FR | 2722973 | 2/1996 |
| SU | 1438759 | 11/1988 |
| WO | 9508969 | 4/1995 |

OTHER PUBLICATIONS

Derwent English Abstract of SU 143–8759 Dated Nov. 23, 1988.
English Abstract of DE 29514984 Dated Oct. 10, 1996.
English Abstract of FR 2722973 Dated Feb. 2, 1986.
Schmidt–Nowara, W., Lowe, A., Wiegand, L., Cartwright, R., Perez–Guerra, F., Menn, S., "Oral Appliances for the Treatment of Snoring and Obstructive Apnea: A Review," *Sleep* 18(6):501–510 (1995).

* cited by examiner

*Primary Examiner*—Michael A. Brown
(74) *Attorney, Agent, or Firm*—Townsend and Townsend and Crew LLP

(57) ABSTRACT

A mandibular advancement device is disclosed. The upper jaw (12) has fitted to it an upper plate (30). The upper plate (30) is firmly received, and generally comprises a body component (32) and two opposed flange components (34), are located to be lying in an area beside and close to the posterior teeth, and particularly the buccal side of the upper posterior teeth. The leading edge (36) of the flanges (34) provide engagement surfaces complementing the engagement surfaces of the trailing edges (26) of the lower flanges (24). The relative lengths of the respective trailing edges (26) and leading edges (36) ensure that mandibular advancement is maintained over a desired range of jaw openings. The angle of inclination of the engaging edges (26, 36) provides a jaw opening path generally arcuate with the protrusive border path.

44 Claims, 14 Drawing Sheets

MANDIBULAR ADVANCEMENT DEVICE

FIELD OF THE INVENTION

This invention relates to a mandibular advancement device that has application in the treatment of orthodontic conditions, snoring, obstructive sleep apnea (OSA) and certain temporomandibular joint disorders.

BACKGROUND OF THE INVENTION

It is generally thought that snoring and OSA occur when there is at least partial occlusion of the airway and that the tongue is involved in this. Snoring and OSA commonly occur during sleep. Mandibular advancement devices advance the lower jaw carrying the tongue forward thereby reducing the likelihood of the tongue impacting on the airway.

Numerous forms of mandibular advancement device are known. One example can be found in International Publication No. WO 95/19746 (PCT/CA95/00009), in the name of The University of British Columbia, which discloses a mandible repositioning appliance formed by an upper bite block (16) and a lower bite block (18) interconnected by an extendible connector (26). The arms (40,42) that join the lower and upper bite blocks extend from a location proximate the lower incisors rearwardly at an inclined angle, to be anchored in the roof of the mouth. There is thought to be a disadvantage with this arrangement, in that the connector (26) and attachment arms (30,32,40,42) intrude excessively into the oral cavity, and the resulting interference may limit efficacy and/or it may be progressively less effective with increasing mouth opening, or it may not permit jaw opening. It is also thought that the bulk of the connectors (50 and 52) embedded in the lower bite block and the limitation to jaw closure may limit compliance.

It is useful at this point to make reference to a terminology relating to mandibular movement that is adopted in this specification, and particularly the discussion of "Border Movements" presented in the text *Handbook of Orthodontics for the Student and General Practitioner*, by Dr Robert E Moyers, published by Year Book Medical Publishers Incorporated of 35 Fast Wacker Drive, Chicago, Ill., U.S.A., Third Edition, Section 1, Part D, pages 148–151. As shown in FIG. V-10, sagittal mandibular movement occurs within a range limited by the border movements, broadly characterised by the most protruded path of opening and closure, the maximal open position of the mandible, the occlusal positions and the most retarded path of closure. In this sense, a reference herein to mandibular advancement represents locating of the mandible so that it functions in the protruded range from the reflex or habital path of closure (occurring between the intercuspal occlusal position and the maximum open position) to the protrusive border path.

SUMMARY OF THE INVENTION

It is an object of the present invention to provide a mandibular advancement device that provides advancement of the lower jaw, and permits freedom of sagittal jaw movement (ie. jaw opening) while retaining advancement within a range protruded from the reflex or habitual path of closure.

It is a further, preferred object for embodiments of the invention to provide a mandibular advancement device which can permit closure to the protruded occusal position.

It is a further, preferred object for embodiments of the invention to provide a mandibular advancement device which can be adjustable to give a variable extent of advancement of the lower jaw.

It is a yet further, preferred object for embodiments of the invention to provide a mandibular advancement device having minimal interference with the tongue, the oral airway, mouth seal and the fundamental tongue space.

The invention provides a mandibular advancement device for the treatment of Obstructive Sleep Apnea and/or snoring, comprising:

at least one lower engagement member having an attachment structure adapted to be releasably attachable to at least a portion of the lower jaw and an engagement surface extending upwardly from said attachment structure; and at least one upper engagement member having an attachment structure adapted to be releasably attachable to at least a portion of the upper jaw and an engagement surface extending downwardly from said attachment structure; and wherein, when fitted to a patient, the lower and upper engagement surfaces are adapted to engage at a location lying in an area beside and close to the posterior teeth in a manner to cause advancement of the lower jaw from the reflex path of opening and to maintain the engagement and advancement, while permitting sagittal movement, up to the normal range of jaw opening extending from an advanced occluding position.

In one particular preferred form, there are two lower engagement members and two corresponding upper engagement members. The upper and lower engagement surfaces are located on either the buccal sides or the lingual sides of the posterior teeth.

In one particular embodiment the upper and lower engagement surfaces can be essentially edge-like. The antagonist surfaces can be arranged so that their engagement is generally arcuate with the protrusive border path over the normal range of jaw opening. The engagement surfaces can be relatively positionally adjustable, for example by use of a screw extension device, to give a variable extent of advancement of the lower jaw in the horizontal plane. The shape of the engagement surfaces can be chosen to provide a variable extent of advancement over the range of opening to depart from the arc of the protrusive border path.

In another form there is a single upper attachment structure and a single lower attachment structure that respectively are in the form of plates, with two engagement surfaces extending therefrom. There can be an elastic lining arranged to closely adapt to the respective dentition.

Advantageously, the respective lower jaw plate and upper jaw plate are shaped to closely adapt to the lower and upper dentition.

The advancement device can be fitted when the lower jaw is at the maximum open position.

In another form, there is provided a mandibular advancement device as defined above, except either the upper or lower engagement member are replaced physically and in function by the buccal surface of the upper dentition or the lingual surface of the lower dentition, respectively.

The invention further discloses a kit of parts, or spare parts comprising a lower engagement member and/or an upper engagement member as those members are defined above.

The invention further discloses a method that has application in the treatment of obstructive sleep apnea and/or snoring, comprising the steps of:

releasably fitting a mandibular advantage device, having upper and lower jaw components, to a patient, the components engaging at a location in an area beside and close to the posterior teeth and causing advancement of the lower jaw from the reflex path of opening; and maintaining engagement and advancement, while permitting sagittal movement, up to the normal range of jaw opening extending from an advanced occluding position.

Embodiments of the invention offer advantages over prior art arrangements. Firstly, lower jaw advancement is achieved both when the jaw is closed and over a range of jaw openings, meaning that the therapeutic affect can be achieved in the presence of jaw closure and opening. Also, advancement is retained for all extents of mouth opening, tending to ensure treatment efficacy.

A corollary is that a patient is able to have an unrestricted range of jaw movement from open to almost closed. Because the patient is able to perform these movements without restriction, this may lead to increased compliance with the treatment. Freedom of opening of the lower jaw also allows the user to yawn and perform other functions such a licking of the lips.

Further advantages are that the location of the engagement members means that speech and aethetics are only minimally affected.

Patients can be intolerant of artificial bite opening. Thus the zero or minimal bite opening in the protruded occlusal position may result in improved tolerance and compliance with treatment. With zero or minimal bite opening the important function of swallowing is facilitated. The user also is more likely to have upper to lower lip seal reducing mouth and throat desiccation and perhaps helping in stabilisation of the mandible and tongue. These effects may result in improved efficacy tolerance and compliance with treatment.

The positioning of the engagement surfaces close to and beside the posterior teeth is such as to not impact on the airway, or the active area of the tongue significantly. This is important in promoting patient compliance with the treatment, as any impingement on the oral route of respiration can increase the velocity and turbulence of orally inspired air resulting in lowered air temperature and oral dessication, and can be an actual or perceived impediment to oral respiration. Also, artificial bite opening or encroachment on oral tongue space may cause the tongue to encroach on the pharyngeal airway. Furthermore, the positioning of the engagement members beside the upper and lower posterior teeth allows the engagement surfaces to be sufficiently long to ensure protrusion over any degree of jaw opening likely to occur, and there is no limitation to jaw closure.

BRIEF DESCRIPTION OF THE DRAWINGS

Embodiments of the invention now will be described with reference to the accompanying drawings, in which.

DETAILED DESCRIPTION OF EMBODIMENTS AND BEST MODE

Figure 1:
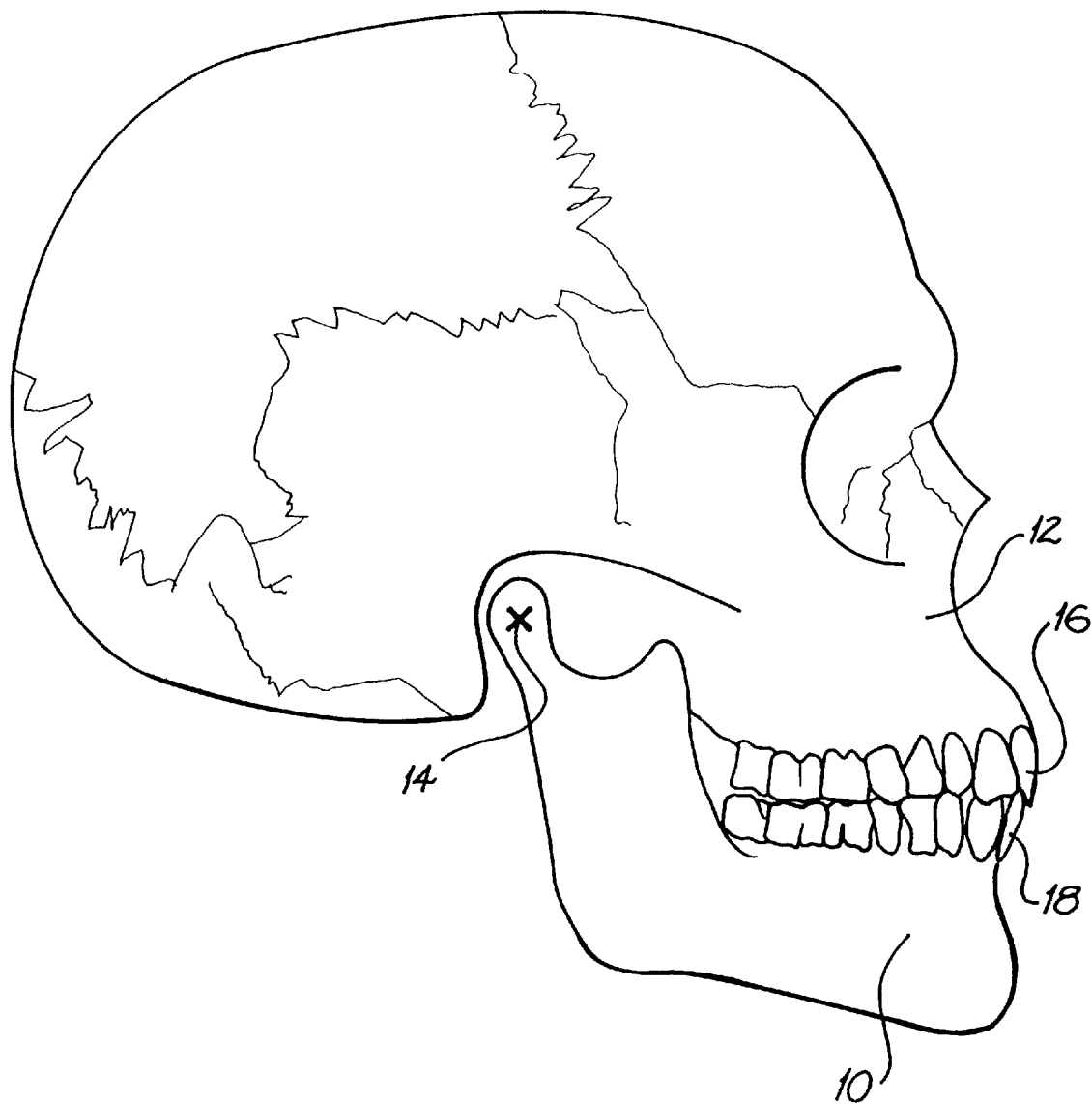
FIG. 1 shows a side view of the human skull with the lower jaw closed.

In FIG. 1, the normal bite (occlusal) position for the teeth is shown, and particularly the relationship between the upper incisors 16 and the lower incisors 18. In performing mandibular advancement treatment, it is desired to advance a lower jaw 10 to a position relative to the upper jaw 12 as shown representatively in FIG. 2a. The degree of advancement can depend upon clinical requirements. The relative displacement of the hinge point 14 can be seen to have both horizontal and vertical components. Advancement of the lower jaw 10 carries the tongue forward so that (particularly in sleep) there is a greatly reduced tendency for the tongue to impinge on the pharynx. The degree of advancement can be from the reflex or habitual closing path to the anterior border path.

Figure 2A:
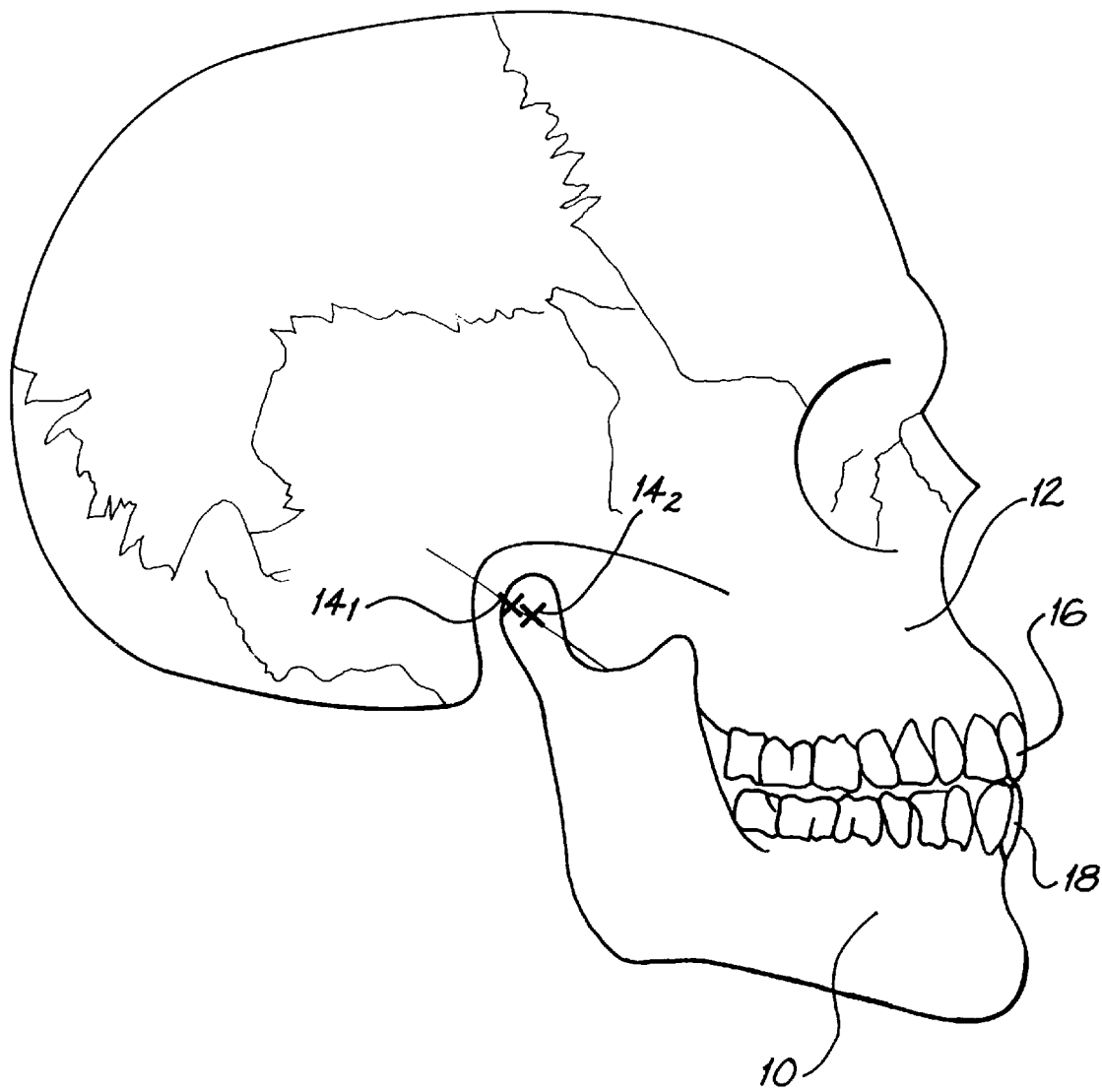
FIGS. 2a and b show a side view of the skull with the lower jaw advanced.
Figure 2B:
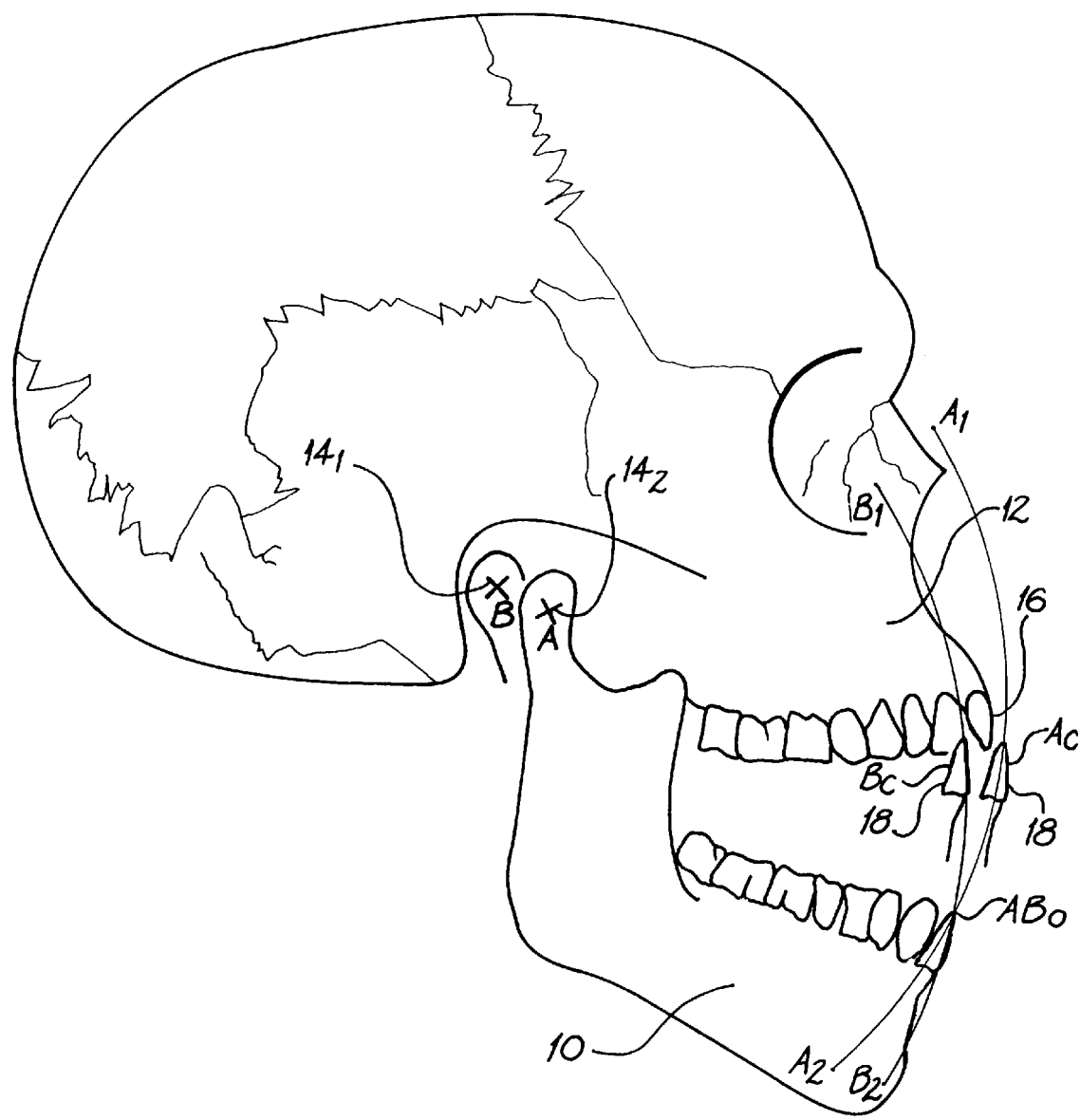

FIG. 2b shows the relative location of the lower jaw for degrees of jaw opening and advancement. Line $A_1A_2$ represents the arc of opening from tile fully protruded position centred on the point $A_x$. Line $B_1$-$AB_0$-$A_2$ is the path of opening from the habitual or reflex closed position, centred on point $B_x$ translating to $A_x$. The point $AB_0$ represents the lower incisor tip at maximal opening on both paths $A_1A_2$ and $B_1$-$AB_0$-$A_2$. The point $B_c$ represents the position of the lower incisor tip closed in the habitual or reflex position. The point $A_c$ represents the position of the lower incisor tip closed in the maximally protruded fully closed position. The area bounded by the points $B_c$-$A_c$-$AB_0$ is that available for advancement of the mandible.

Figure 3:
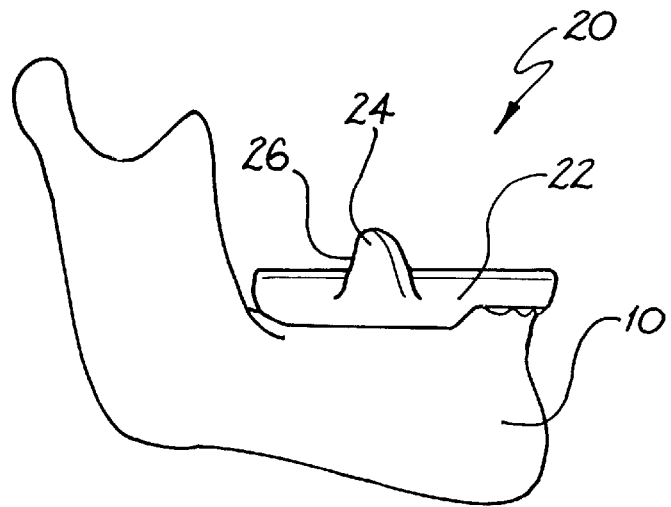
FIG. 3 is a perspective view of a lower plate fitted to the lower dentition.

FIG. 3 shows detail only of the lower jaw 10. A lower plate 20 is received and firmly fitted over the lower teeth. The plate 20 is pre-moulded into a shape to match the lower dentition. The lower plate 20 has a body component 22 and two opposed upstanding flange components 24. Only one of the matching pair of flanges 24 can be seen in FIG. 3, the left side flange not being shown for reasons of clarity. The flange components 24 are located to be lying in an area beside and close to the posterior teeth, and particularly the buccal side of the lower posterior teeth. The trailing edge 26 of each flange 24 forms an engagement surface, the function of which will presently be described.

Figure 4:
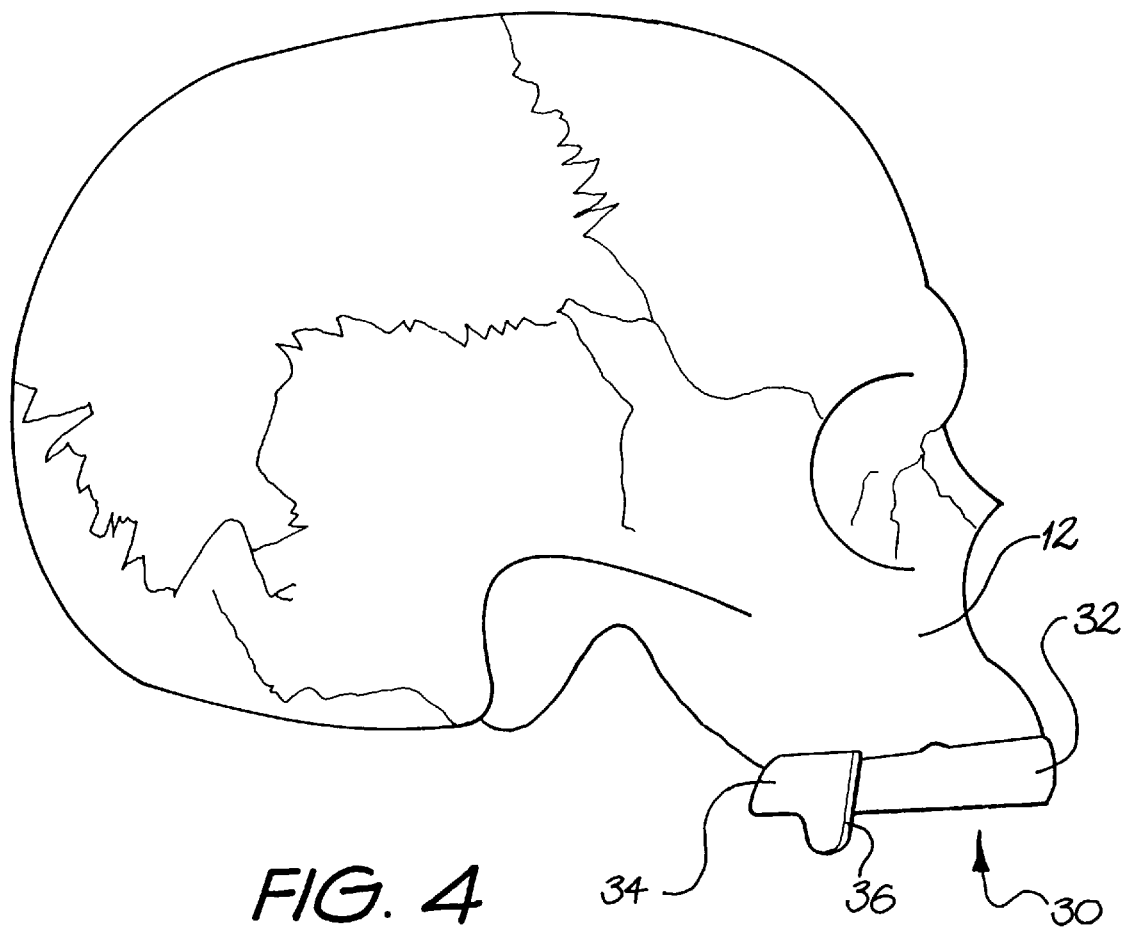
FIG. 4 is a perspective view of an upper plate fitted to the upper dentition.

FIG. 4 is a partial side view of the skull omitting the lower jaw. The upper jaw 12 has fitted to it an upper plate 30. The upper plate 30 is firmly received, and generally comprises a body component 32 and two opposed flange components 34, only one of which is shown for clarity. The upper flange components 34 are located to be lying in an area beside and close to the posterior teeth, and particularly the buccal side of the upper posterior teeth The leading edge 36 of the flanges 34 provide engagement surfaces complementing the engagement surfaces of the trailing edges 26 of the lower flanges 24.

Figure 5:
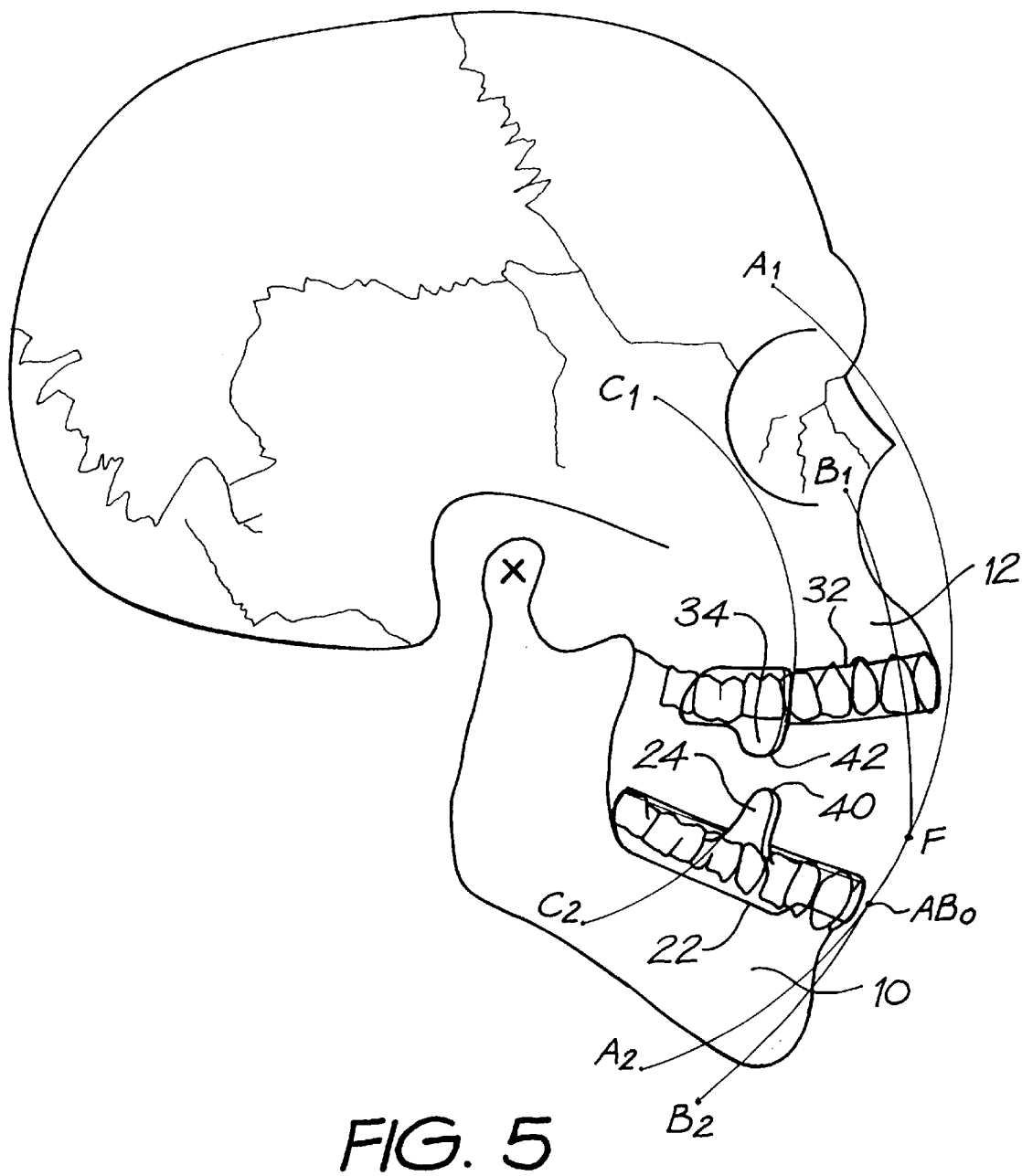
FIG. 5 is a side view showing the advancement device being fitted.

FIG. 5 shows the lower jaw at an extreme open position, in which configuration the lower plate 20 and the upper plate 30 can be fitted to the respective dentition. FIG. 5 also includes a number of schematic lines showing paths of jaw movement, similar to FIG. 2b. Line $A_1A_2$ is the arc of opening from the fully protruded position. Line $B_1$-F-$AB_0$-$B_2$ is the path of opening from habitual or reflex closed position. Line $C_1C_2$ is the schematic plane of the engagement surfaces arcuate with $A_1A_2$ centred on point $A_x$. The representation is artificially exaggerated in that the lower jaw 10 cannot normally extend to the degree of opening shown. The degree of opening is sufficient for the tip 40 of the lower flanges 24 to clear the tip 42 of the respective upper flanges 34 so that the respective plates can be freely fitted. This range is represented by the arc segment F-$AB_0$. The lengths of the respective leading edges 36 and trailing edges 26 are chosen to satisfy this geometry. They can be shorter in length if the engagement is not required to cover the full range from the habitual closed position to point F. In this configuration it would be usual for the upper plate 30 to be fitted first.

Figure 6:
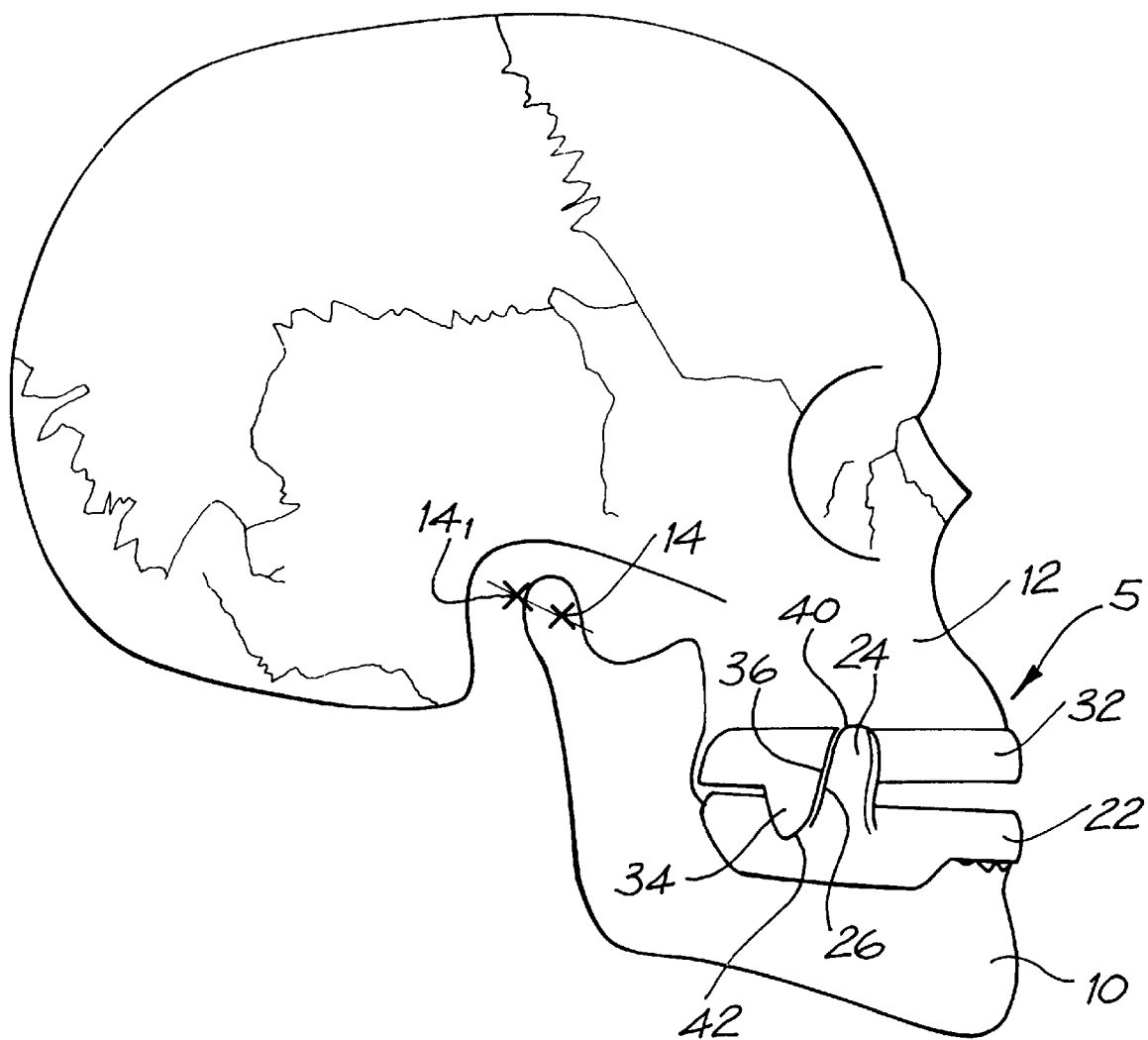
FIGS. 6 and 7 are side views showing the advancement device in use.

FIG. 6 shows the jaws in the partially closed position, in which state the trailing edge 26 of the lower flanges 24 engage the leading edge 36 of the upper flanges 34; this mechanical engagement advances and maintains the lower jaw in an advanced range as also shown in FIGS. 2a and 2b.

The location of engagement of the upper and lower flanges 24,34 only minimally impinges upon the airway, or active tongue space. The relative location of the flanges 24,34 is in the beside and close to the posterior teeth means that they are closer to the hinge point than are the incisors, and as such can be of a relatively shorter length to ensure mandibular advancement for a given arcuate range of jaw opening.

Figure 7:
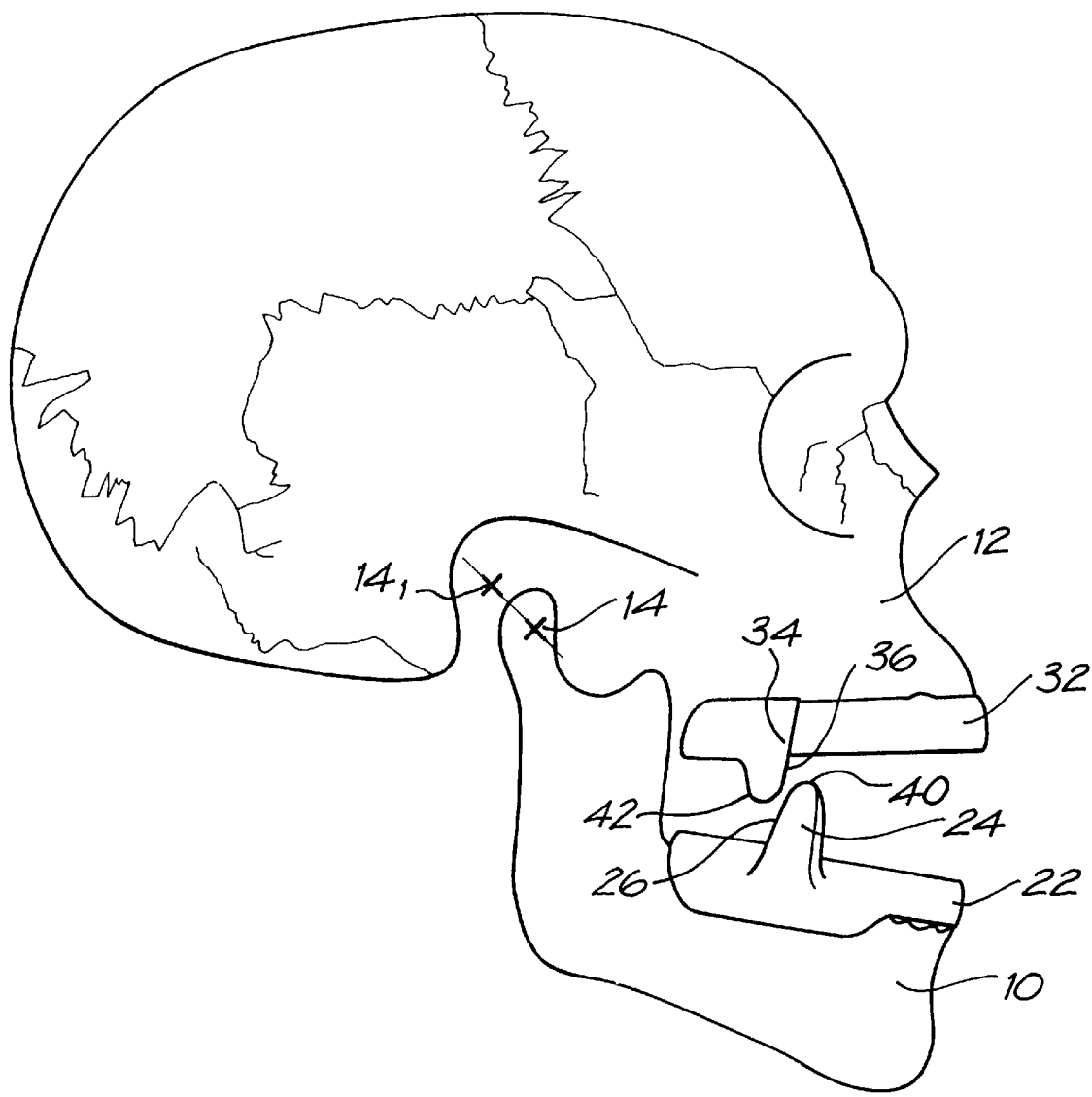

As also noted above, the relative lengths of the respective trailing edges 26 and leading edges 36 ensure that mandibular advancement is maintained over a desired range of lower jaw openings, a near extreme case of which is shown in FIG. 7. The angle of inclination of the engaging edges 26,36, is such as to provide a jaw opening path generally arcuate with the protrusive border path.

The mandibular advancement device 5 embodying the invention can have a number of beneficial uses, including as an early interceptive device to encourage mandibular growth, in the treatment of certain orthodontic problems, in the treatment of certain temporomandibular joint problems, in the management of bruxism, and in the treatment of snoring and obstructive sleep apnea.

The device 5 can be formed from orthodontic materials such as acrylic, cobalt chromium, gold, silver, platinum or other acceptable materials. A typical fabrication procedure first involves taking a casting or impression of the patient's upper dental structures from which a plaster model is made. This is repeated for the lower dental structures. A bite registration is taken with the lower jaw in the desired advanced position, requiring a patient to close into the desired advanced position. The upper and lower teeth plaster models are located into the bite registration, then the assembly mounted on an "articulator" which simulates jaw motion. A registration of the jaw relationship at maximal opening is made and also transferred to the articulator. With the articular thus set, the models and bite registration are demounted. The base plates are cast in a dental acrylic of choice in a conventional dental manner with clasps for retention if indicated. Palatal coverage can be minimised. The base plates could instead be fabricated using a pressure and thermal formed dual laminate with an elastic liner and a hard outer shell of a type compatible with cold cure processed acrylic.

The upper and lower plates then are remounted on the articulator in the recorded advanced position. Any interference by the base plates to complete closure in the protruded contact position is eliminated if deemed clinically necessary. The upper and lower flanges and appropriate but minimised upper to lower baseplate occlusual support are formed using cold cure processed acrylic. The engaging surfaces are formed lateral to the molars. They are formed to the predetermined degree of advancement and contoured to parallel the protrusive border path. When the engaging surfaces are lateral to the dentition the lower flanges project up from the lower device, and the engagement takes place predominantly lateral to the upper dentition. Lateral movement can be provided by laterally spacing each lower flange from the upper baseplate by about 0.75 mm each side. The registration of the jaw relationship at maximal opening is used to ensure that the engagement surfaces are sufficiently long to prevent unwanted disarticulation of the engagement surfaces, yet not so long as to cause difficulty of insertion or removal. A final functional check is made prior to demounting the device from the articulator. The device is trimmed and polished for issue to the patient.

Figure 8:
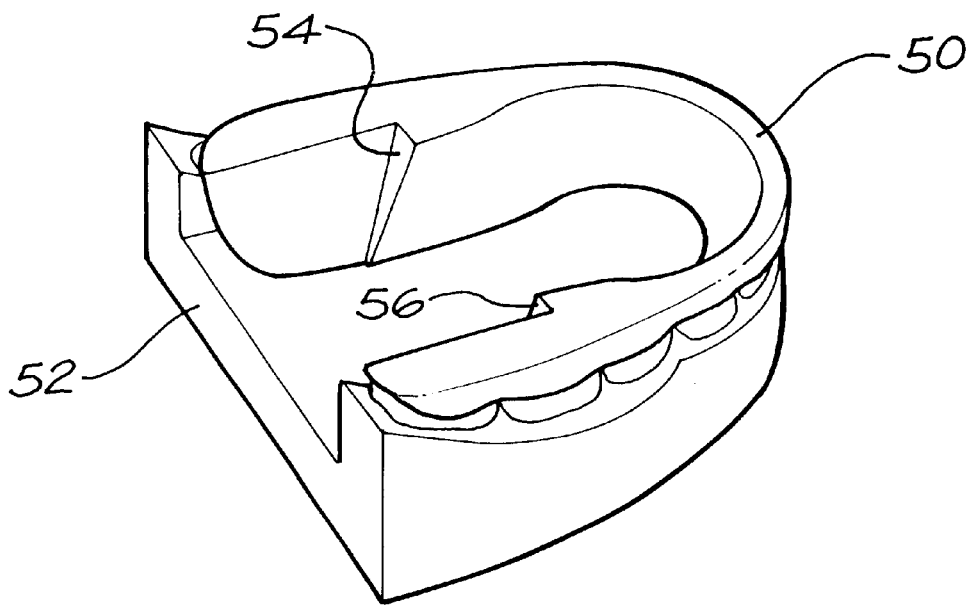
FIGS. 8 to 10 show further embodiments of a lower plate.

FIG. 8 shows a further embodiment of a lower plate 50, in this case fitted over its plaster model 52 representing the manner in which the plate would be worn on the lower dentition. In this arrangement, the engagement surfaces are formed beside and close to the lingual sides of the lower posterior teeth in the manner of integral inclined surfaces 54,56.

Figure 9:
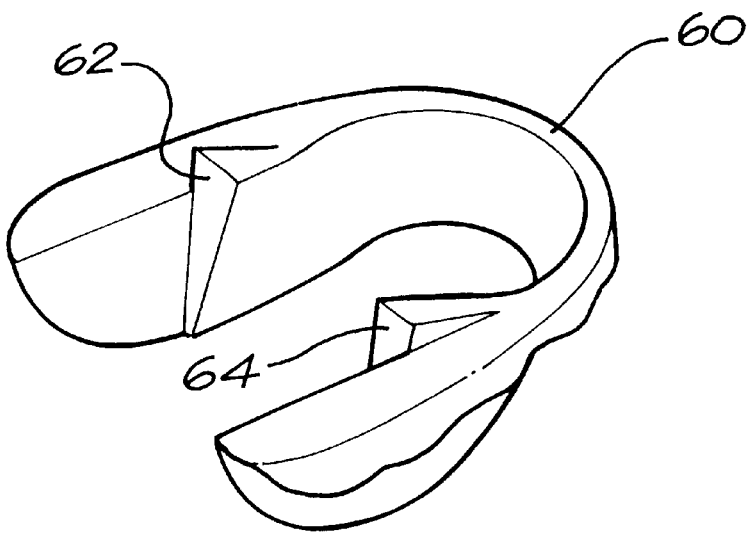

FIG. 9 shows a further embodiment of a lower plate 60 similar to that shown in FIG. 8. Here, the engagement surfaces also are formed by inclined surfaces 62,64, and extend above the top-most level of the plate providing for mandibular advancement for an increased range of jaw opening than the arrangement shown in FIG. 8.

The embodiments of both FIGS. 8 and 9 are such as not to impinge upon the active tongue space, especially when the flanges of the upper component are in situ, even though they reside to the inside of the lower dentition.

Figure 10:
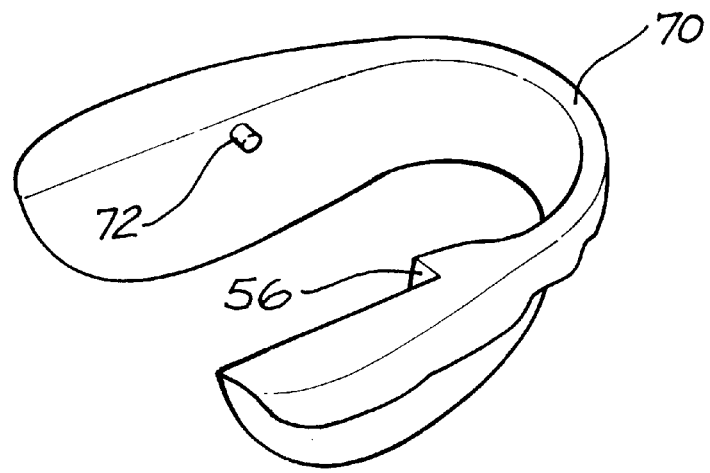

FIG. 10 shows a yet further embodiment of a lower plate 70 showing, on one side, an inclined surface 56, and on the other side another form of engagement surface formed as a peg or protrusion 72. It usually would be intended that a peg is used bilaterally (ie. as a pair). The protrusion can be made from a suitable orthodontic wire otherwise securely embedded in the base plate 70. Similarly the antagonist engagement member of the upper plate can be made of a suitable metal flange otherwise securely embedded in the antagonist base plate.

Figure 11:
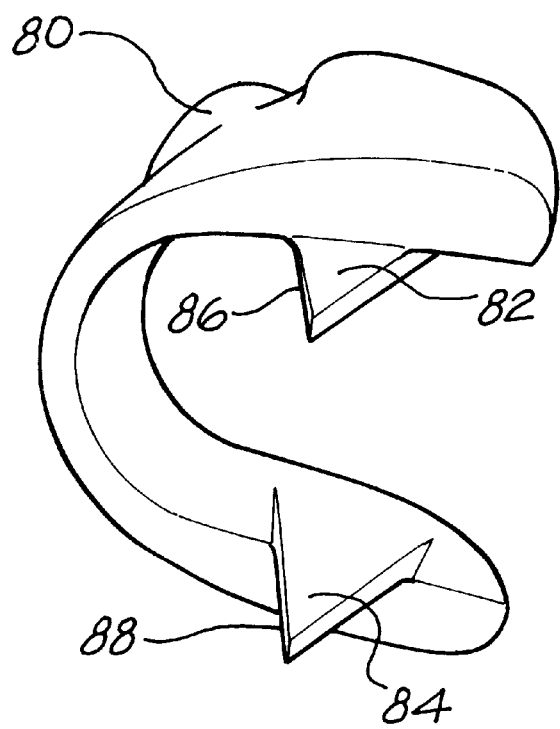
FIG. 11 shows a further embodiment of an upper plate.

FIG. 11 shows another embodiment of an upper plate 80. The upper plate 80 is intended for use with the forms of lower plate 50, 60, 70 described above with reference to FIGS. 8, 9 and 10. The upper plate 80 has extending from the inner (lingual) side of the dentition a pair of downwardly directed flanges 82,84 that, when the lower and upper plates are worn, engage to advance the lower jaw by means of the respective leading edges 86,88 engaging with the inclined surface 54,56,62,64 or the peg 72.

Figure 12:
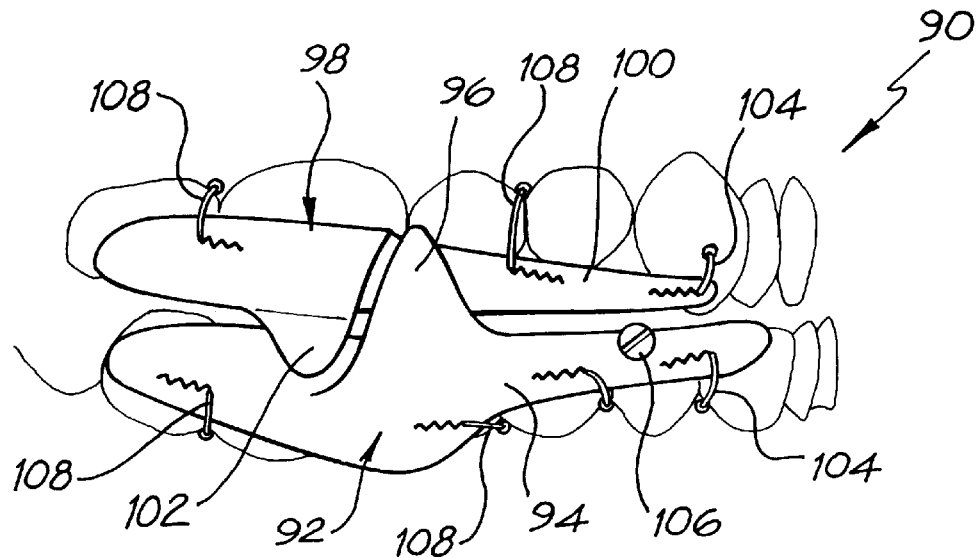
FIGS. 12 and 13 show alternative advancement devices.

FIG. 12 shows the jaws slightly open with a yet further embodiment of an advancement device 90 that is similar to that shown in FIGS. 3–7, and comprises a lower plate 92 having a body portion 94 and an upstanding flange 96. Similarly, there is an upper plate 98 having a body portion 100 and a downwardly extending flange 102. In other embodiments, the flange 102 may not extend downwardly to the extent shown. The trailing edge of the lower flange 96 engages the leading edge of the upper flange 102 to provide for lower jaw advancement. Here, the suitably strengthened upper and lower plates 92,98 extend anteriorally only along the inside of the upper and lower anterior teeth leaving the incisors exposed. The respective body portions 94,100 include anchored hooks 104 if clinically required to receive vertical elastic bands. In this embodiment a number of clasps 108 hold the devices firmly in place. The lower body portion 94 also includes a rebated screw 106 that can be advanced to engage the underside of the body portion 100 of the upper plate 98 to provide anterior support and/or canine guidance if required. The screw 106 is located in approximately the canine position.

Figure 13:
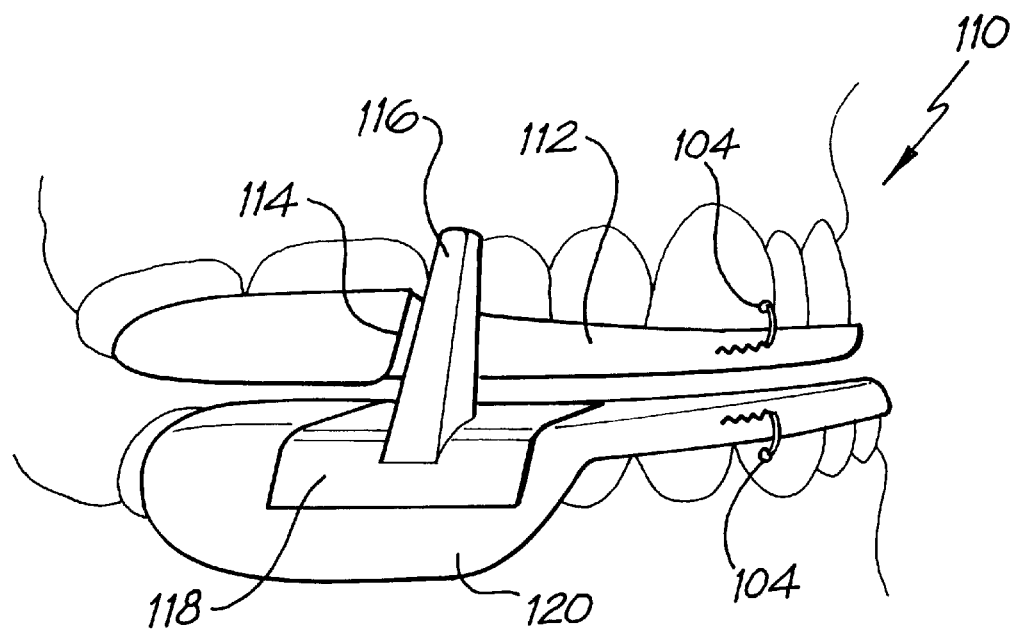

FIG. 13 shows a yet further embodiment of a mandibular advancement device 110. The upper plate 112 includes an inclined surface 114 against which can engage an upstanding blade 116 that extends from a base plate 118. The base plate, in turn, is affixed to the lower plate 120. In this embodiment the base plate 118 and the blade 116 are performed from a material such as cobalt chromium. The base plate 118 can be fixed to the lower plate 120 by any convenient means, including being embedded within plastics materials so that the blade 116 protrudes therethrough. Again, hooks 104 are provided for elastics if required, as can clasps.

Figure 14A:
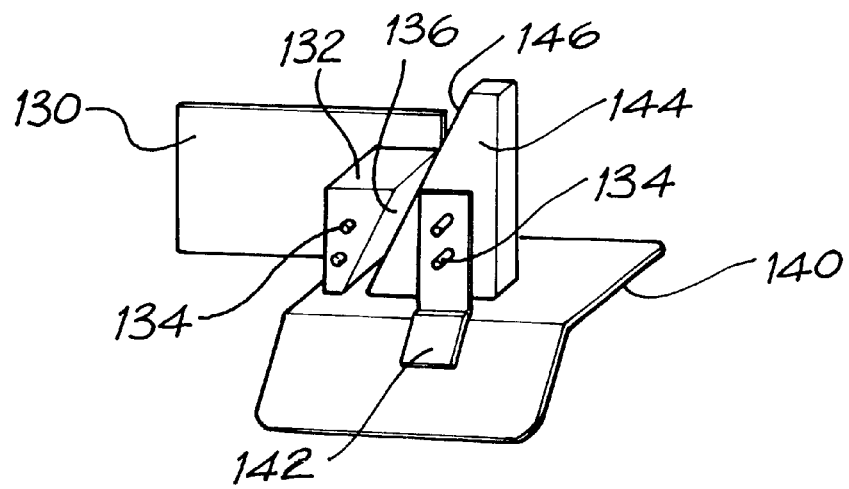
FIGS. 14a and b show alternative arrangements of components forming engagement surfaces.

FIG. 14a shows a further arrangement for the provision of the engaging surfaces to provide advancement and other effects. A plate component 130, intended to be received within an upper plate as previously described, includes a removable block 132 fixed thereto by pins 134 or other suitable means. The block 132 includes an angled leading edge 136 forming an engagement surface. In a similar manner, a lower base plate component 140 has a tag 142 extending from it which receives a removable block 144 affixed thereto by similar pins 134. The trailing edge 146 of the block 144 provides the matching engagement surface with the leading edge 136 of the upper block 132. Alternatively, either one of the blocks 132,144 can be fixed or non-removable to still retain the desired advancement over the range of opening.

Figure 14B:
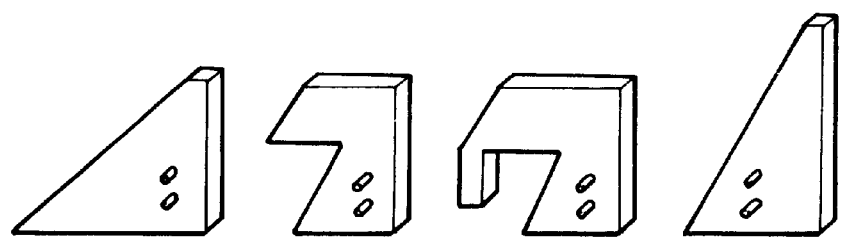
Figure 14B:
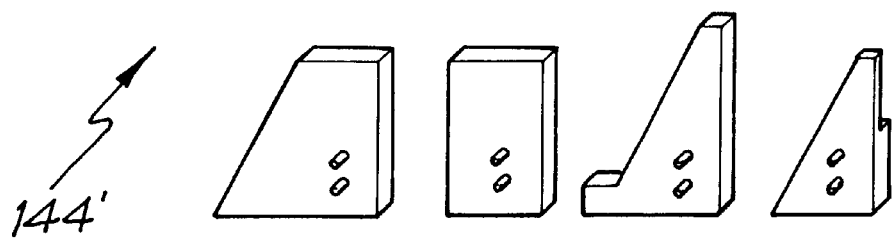

FIG. 14b shows examples of other arrangements for the engagement block 144', which can be chosen by a clinician or modified depending upon clinical requirements. The shapes provide differing degrees of advancement with jaw opening, such that the path of advancement with opening departs from the arc of the border path.

Figure 15A:
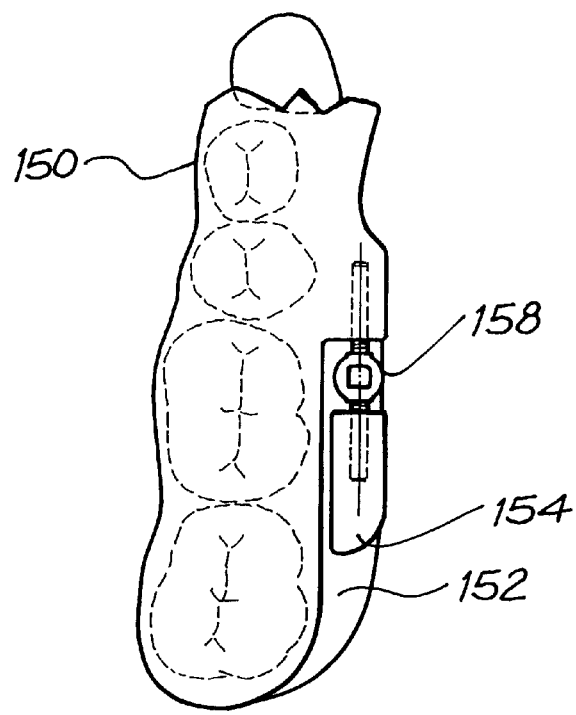
FIGS. 15a and b respectively show a top view and side view of a lower jaw plate having progressive advancement of the engagement surface.
Figure 15B:
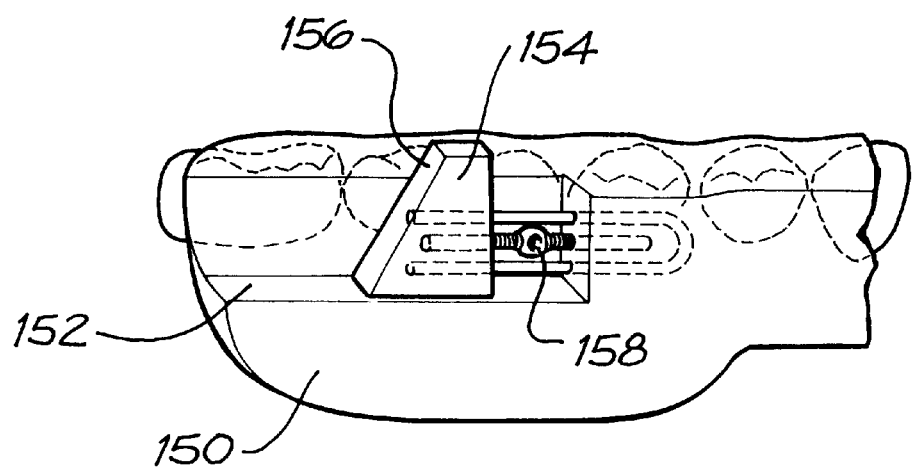

An alternative to providing replaceable blocks of different sizes to achieve the required degree of advancement is shown in FIGS. 15a and b. This embodiment is a modification of the lower plate 20 as shown in FIG. 9. These figures respectively show a portion of the lower plate 150 representing a top view and an inside view of the left hand side of the lower dentition. A recess 152 is provided in the inside or lingual surface of the lower plate 150 along the bottom surface of which slides an adjustable block 154, the trailing edge 156 of which is intended to engage a flange such as that shown in items 82,84 in FIG. 11. The location of the block 154 controls a degree of mandibular advancement. Adjustability is provided by a turnbuckle mechanism (or jack screw mechanism) 158 which can be operated by a turnbuckle key to advance or retract the block 154 as desired. In this way, the appropriate treatment can be provided as determined by the clinician.

In all of the embodiments previously described where a plate was utilised, it is equally possible for a plate to be used such that fits the dental structures and is anchored to the teeth by clasps or other means. Such a plate or framework can be modified to include extending pegs or protrusions to form an engagement surface contacting with an engagement surface of the plate or framework in the antagonist jaw.

Figure 16A:
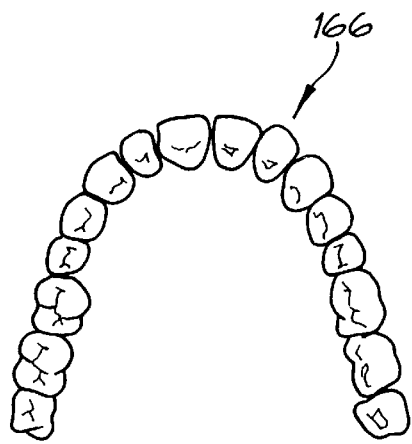
FIGS. 16a–d and 17a–d show yet further alternative advancement devices.
Figure 16B:
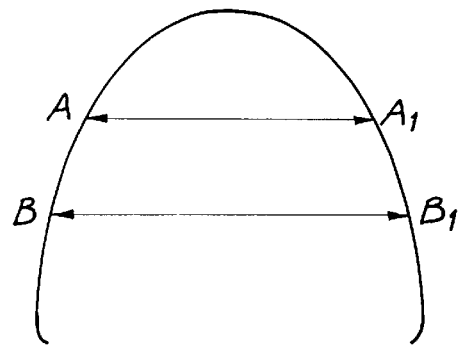
Figure 16C:
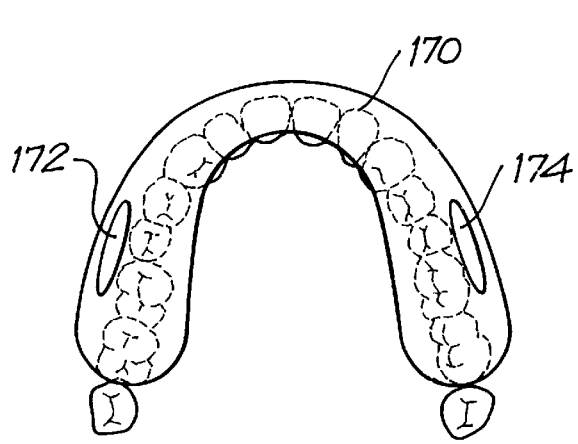
Figure 16D:
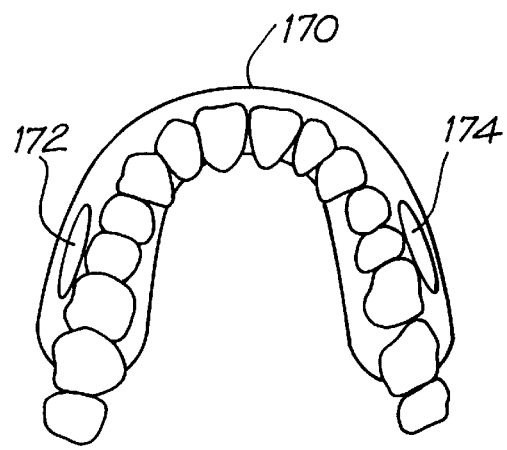

FIG. 16a shows an underside view of the upper dentition 166. The buccal surface of the upper dentition is represented by the trace in FIG. 16b. A taper naturally occurs as is represented by the lines between points $A-A_1$, and points $B-B_1$. This tapering geometry can be used advantageously as an engagement surface in the manner described with reference to the earlier embodiments. FIG. 16c shows a plate 170 fitted to the lower dentition. The upstanding flanges 172,174 extend from the lower plate, and it is these that engage with the buccal sides of the upper dentition in the region of the posterior teeth. FIG. 16d shows a top view looking through the upper teeth 166 where the flanges 172,174 have engaged against the upper dentition, for example, in the region between points A–B and $A_1-B_1$. Advancement of the lower jaw is achieved in that the flanges 172,174 are not able to retreat by virtue of the outwardly tapering shape of the buccal sides of the upper posterior dentition. The relative location of the flanges 172,174 in the lower plate 170 thus will determine the degree of advancement.

Figure 17A:
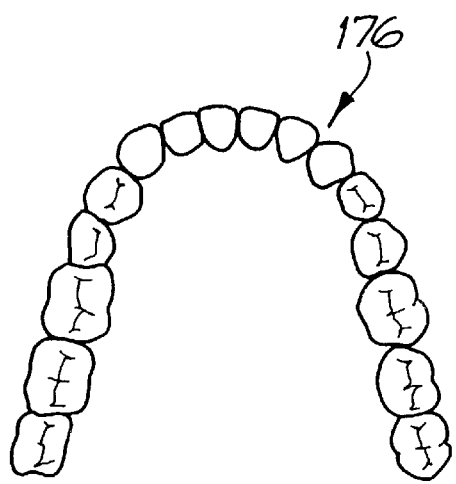
Figure 17B:
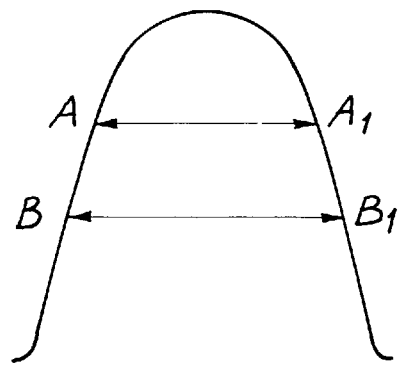
Figure 17C:
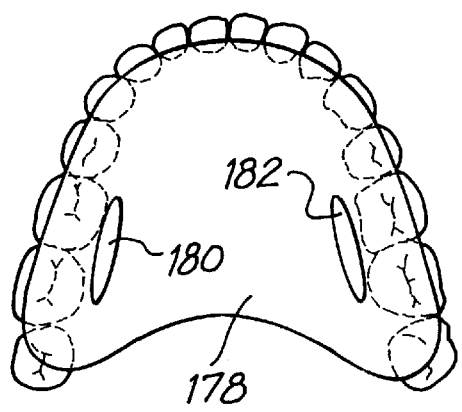
Figure 17D:
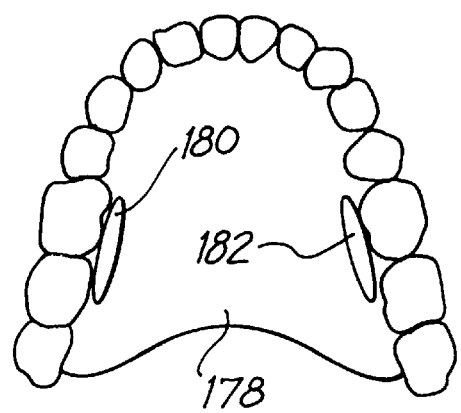

FIGS. 17a–d show a related embodiment. In FIG. 17a, a lower dentition 176 is shown, together with a trace of the lingual surface of a lower dentition represented by FIG. 17b5. The taper of the surface can be seen from the different distances between points $A-A_1$ and the points $B-B_1$. FIG. 17c shows a plate 178 fitted to the upper dentition, and from which two downwardly extending flanges 180,182 extend. FIG. 17d is a view looking upwardly through the lower teeth so that the upper plate 178 can be partly seen, as can the engagement of the flanges 180,182 with the lingual sides of the lower dentition in the region of the posterior teeth, and, for example, between points A–B and $A_1-B_1$. Advancement of the lower jaw is achieved in that it is not possible for the jaw to retreat because of engagement of the flanges 180,182 with the lingual sides.

It may be desirable to add a simple tooth-stabilising plate, such as a retainer fitted to the antagonistic arch. This may serve to resist movement of the teeth due to engagement of the respective flange, and also may avoid a degree of discomfort.

Numerous alterations and modifications can be made without departing from the inventive concept. All such modifications and alterations are to be considered as incorporated herein. For example, the use of flanges can be replaced by the use of pegs, or the like, and any arrangements shown having engagement beside the buccal sides of the posterior teeth can equally be on the lingual sides, and vice versa.

What is claimed is:

1. An advancement device for the treatment of obstructive sleep apnea and/or snoring, comprising:
    at least one lower component having an attachment structure that is releasably attachable to at least a portion of the lower jaw and an engagement surface extending upwardly from said attachment structure; and
    at least one upper component having an attachment structure that is releasably attachable to at least a portion of the upper jaw and an engagement surface extending downwardly from said attachment structure; and
    wherein, when the lower and upper engagement members are fitted to the jaws of a patient for use in sleep, the lower and upper engagement surfaces engage at a location lying in an area beside and close to the posterior teeth in a manner to cause advancement of the lower jaw from the reflex path of opening and maintain the engagement and advancement, while permitting sagittal movement, up to the normal range of jaw opening extending from an advanced occluding position by remaining fitted to the jaws of the patient when in use.

2. An advancement device according to claim 1, wherein there are two lower engagement surfaces and two corresponding upper engagement surfaces.

3. An advancement device according to claim 2, wherein the upper and lower engagement surfaces are located on either the buccal sides or the lingual sides of the posterior teeth.

4. An advancement device according to claim 3, wherein the upper or lower engagement surfaces substantially define an edge.

5. An advancement device according to claim 4, wherein the lengths of the upper and lower engagement surfaces determine the range of jaw opening over which engagement is maintained.

6. An advancement device according to claim 5, wherein the engagement surfaces are shaped to proscribe an opening path generally arcuate with the protrusive border path over the normal range of jaw opening.

7. An advancement device according to claim 3, wherein either the upper or lower engagement surface defines an edge of contact and the corresponding lower or upper engagement surface defines a point of contact.

8. An advancement device according to claim 7, wherein the length of the engagement surface defining the edge of contact determines the range of jaw opening over which engagement is maintained.

9. An advancement device according to claim 2, wherein the engagement surfaces are relatively positionally adjustable to give a variable extent of advancement of the lower jaw.

10. An advancement device according to claim 9, wherein said positional adjustment is achieved by a screw extension device associated with one or more of said engagement surfaces.

11. An advancement device according to claim 10, wherein the shape of the engagement surfaces provides a variable extent of advancement over the range of opening to depart from the arc of the protrusive border path.

12. An advancement device according to claim 2, wherein at least one of said upper attachment structure and said lower attachment structure are in the form of a single dental plate.

13. An advancement device according to claim 12, wherein the at least one single dental plate is shaped to be closely adapted to at least part of the respective dentition.

14. An advancement device according to claim 2, wherein at least one of said upper attachment structure and said lower attachment structure include a single elastic lining arranged to be closely adapted to the respective dentition.

15. An advancement device according to claim 2, wherein at least one of said upper attachment structure and said lower attachment structure include clasps to maintain fitting with the respective dentition.

16. A method for treating obstructive sleep apnea and/or snoring, comprising the steps of:
releasably fitting a mandibular advancement device, having upper and lower components, to the jaws of a patient for use in sleep, the components engaging at a location in an area beside and close to the posterior teeth and causing advancement of the lower jaw from the reflex path of opening; and maintaining engagement and advancement, while permitting sagittal movement, up to the normal range of jaw opening extending from an advanced occluding position by said components remaining fitted to the jaws of the patient when in use.

17. An advancement device for the treatment of obstructive sleep apnea and/or snoring, comprising:
a lower dental plate that is releasably attachable to the lower jaw having left and right upwardly extending flanges located near to and beside the posterior teeth, a trailing edge of each flange forming an engagement surface;
an upper dental plate that is releasably attachable to the upper jaw having left and right downwardly extending flanges located near to and beside the posterior teeth, a leading edge of each flange forming an engagement surface; and
wherein, when said upper and lower plates are fitted to the jaws of a patient for use in sleep, the respective left and right trailing edges and leading edges engage at a location lying in an area beside and close to the posterior teeth in a manner to cause advancement of the lower jaw from the reflex path of opening and to maintain the engagement and advancement, while permitting sagittal movement, up to the normal range of jaw opening extending from an advanced occluding position by remaining fitted to the jaws of the patient when in use.

18. An advancement device according to claim 17, wherein the flanges are located on the buccal sides of the posterior teeth.

19. An advancement device according to claim 17, wherein the flanges are located on the lingual sides of the posterior teeth.

20. An advancement device according to claim 17, wherein at least one of said lower and upper dental plates are in a partial form.

21. An advancement device according to claim 17, wherein at least one of said lower and upper dental plates are in a full form.

22. An advancement device for the treatment of obstructive sleep apnea and/or snoring, comprising:
a lower dental plate that is adapted to be releasably attached to the lower jaw having left and right upwardly extended flanges located near to and beside the posterior teeth, a trailing edge of each flange forming an engagement surface;
an upper dental plate that is adapted to be releasably attached to the upper jaw having left and right integral inclined surfaces located near to and beside the posterior teeth that each form an engagement surface; and
wherein, when said upper and lower plates are fitted to the jaws of a patient for use in sleep, said left trailing edge and left inclined surface, and said right trailing edge and right inclined surface, respectively engage and cause advancement of the lower jaw from the reflex path of opening and maintain the engagement and advancement, while permitting sagittal movement, up to the normal range of jaw opening extending from an advanced occluding position by remaining fitted to the jaws of the patient when in use.

23. An advancement device according to claim 22, wherein the inclined surfaces and the engagement surfaces are located on the buccal sides of the posterior teeth.

24. An advancement device according to claim 22, wherein the inclined surfaces and the engagement surfaces are located on the lingual sides of the posterior teeth.

25. An advancement device for the treatment of obstructive sleep apnea and/or snoring, comprising:
- an upper dental plate that is adapted to be releasably attached to the upper jaw having left and right downwardly extended flange located near to and beside the posterior teeth, the leading edge of each flange forming an engagement surface;
- a lower dental plate that is adapted to be releasably attached to the lower jaw having left and right integral inclined surfaces located near to and beside the posterior teeth that each form an engagement surface; and
- wherein, when said upper and lower plates are fitted to the jaws of a patient for use in sleep, said left leading edge and left inclined surface, and said right leading edge and right inclined surface, respectively engage and cause advancement of the lower jaw from the reflex path of opening and maintain the engagement and advancement, while permitting sagittal movement, up to the normal range of jaw opening extending from an advanced occluding position by remaining fitted to the jaws of the patient when in use.

26. An advancement device according to claim 25, wherein the inclined surfaces and the engagement surfaces are located on the buccal sides of the posterior teeth.

27. An advancement device according to claim 25, wherein the inclined surfaces and the engagement surfaces are located on the lingual sides of the posterior teeth.

28. An advancement device for the treatment of obstructive sleep apnea and/or snoring, comprising:
- a lower dental plate that is adapted to be releasably attached to the lower jaw having left and right upwardly extended flanges located near to and beside the posterior teeth, the trailing edge of each flange forming an engagement surface;
- an upper dental plate that is adapted to be releasably attached to the upper jaw having left and right protrusions located near to and beside the posterior teeth that each form a point of engagement; and
- wherein, when said upper and lower plates are fitted to the jaws of a patient for use in sleep, said left trailing edge and left protrusion, and said right trailing edge and right protrusion, respectively engage and cause advancement of the lower jaw from the reflex path of opening and maintain the fitting, engagement and advancement, while permitting sagittal movement, up to the normal range of jaw opening extending from an advanced occluding position by remaining fitted to the jaws of the patient when in use.

29. An advancement device according to claim 28, wherein the protrusions and the engagement surfaces are located on the buccal sides of the posterior teeth.

30. An advancement device according to claim 28, wherein the protrusions and the engagement surfaces are located on the lingual sides of the posterior teeth.

31. An advancement device for the treatment of obstructive sleep apnea and/or snoring, comprising:
- an upper dental plate that is adapted to be releasably attached to the upper jaw having left and right downwardly extended flanges located near to and beside the posterior teeth, the leading edge of each flange forming an engagement surface;
- a lower dental plate that is adapted to be releasably attached to the lower jaw having left and right protrusions located near to and beside the posterior teeth that each form a point of engagement; and
- wherein, when said upper and lower plates are fitted to the jaws of a patient for use in sleep, said left leading edge and left protrusion, and said right leading edge and right protrusion, respectively engage and cause advancement of the lower jaw from the reflex path of opening and maintain the fitting, engagement and advancement, while permitting sagittal movement, up to the normal range of jaw opening extending from an advanced occluding position by remaining fitted to the jaws of the patient when in use.

32. An advancement device according to claim 31, wherein the protrusions and the engagement surfaces are located on the buccal sides of the posterior teeth.

33. An advancement device according to claim 31, wherein the protrusions and the engagement surfaces are located on the lingual sides of the posterior teeth.

34. An advancement device for the treatment of obstructive sleep apnea and/or snoring, comprising:
- a lower dental plate that is releasably attachable to the lower jaw having means to engage the teeth and having left and right upwardly extending flanges located near to and beside the posterior teeth, the trailing edge of each flange component forming an engagement surface;
- an upper dental plate that is releasably attachable to the upper jaw having means to engage the teeth and having left and right downwardly extending flanges located near to and beside the posterior teeth, the leading edge of each flange forming an engagement surface; and
- wherein, when said upper and lower plates are fitted to the jaws of a patient for use in sleep, said respective left and right trailing edges and leading edges engage at a location lying in an area beside and close to the posterior teeth in a manner to cause advancement of the lower jaw from the reflex path of opening and to maintain the engagement and advancement, while permitting sagittal movement, up to the normal range of jaw opening extending from an advanced occluding position by remaining fitted to the jaws of the patient when in use.

35. An advancement device according to claim 34, wherein the flanges are located on the buccal sides of the posterior teeth.

36. An advancement device according to claim 34, wherein the flanges are located on the lingual sides of the posterior teeth.

37. An advancement device according to claim 34, wherein at least one of said plates is a partial dental plate.

38. An advancement device according to claim 34, further comprising one or more spacers located between biting surfaces of said lower dental plate and said upper dental plate to provide support for the jaws.

39. An advancement device according to claim 38, wherein there are a pair of said spacers fixed to the either dental plate, located in approximately the canine position.

40. An advancement device according to claim 39, wherein said spacers are adjustable to provide a controllable degree of spacing.

41. An advancement device for the treatment of obstructive sleep apnea and/or snoring, comprising an upper plate that is releasably attachable to the upper jaw having left and right downwardly extending flanges located near and to the lingual side of the posterior teeth, and wherein, when said upper plate is fitted to the upper jaw of a patient for use in sleep, the left and right flanges engage the lingual sides of the lower dentition in the region of the posterior teeth and, because of the geometry of the lower dentition, result in advancement of the lower jaw from the reflex path of opening and maintain the engagement and advancement, while permitting sagittal movement, over a range of jaw opening extending from an advanced occluding position by remaining fitted to the upper jaw of the patient when in use.

42. An advancement device according to claim 41, further comprising a tooth stabilizing plate fitted to the lower dentition.

43. An advancement device for the treatment of obstructive sleep apnea and/or snoring, comprising a lower plate that is releasably attachable to the lower jaw having left and right upwardly extending flanges located near and to the buccal side of the posterior teeth, and wherein, when said lower plate is fitted to the lower jaw of a patient for use in sleep, the left and right flanges engage the buccal sides of the upper dentition in the region of the posterior teeth and, because of the geometry of the upper dentition, result in advancement of the lower jaw from the reflex path of opening and maintain the engagement and advancement, while permitting sagittal movement, over a range of jaw opening extending from an advanced occluding position by remaining fitted to the lower jaw of the patient when in use.

44. An advancement device according to claim 43, further comprising a tooth stabilizing plate fitted to the upper dentition.

* * * * *